United States Patent [19]

Sollott et al.

[11] Patent Number: 4,535,193
[45] Date of Patent: Aug. 13, 1985

[54] 1,4,6,9-TETRANITRODIAMANTANE

[75] Inventors: Gilbert P. Sollott, Plymouth Meeting, Pa.; Everett E. Gilbert, Morristown, N.J.

[73] Assignee: The United States of America as represented by the Secretary of the Army, Washington, D.C.

[21] Appl. No.: 586,364

[22] Filed: Mar. 5, 1984

[51] Int. Cl.$^3$ .............................. C07C 79/08
[52] U.S. Cl. .................... 568/941; 568/942
[58] Field of Search ................ 568/941, 942; 149/92, 149/88

[56] References Cited

U.S. PATENT DOCUMENTS

| | | | |
|---|---|---|---|
| 3,053,907 | 9/1962 | Smith et al. | 568/941 |
| 3,258,498 | 6/1966 | Schneider | 568/941 |
| 3,535,390 | 10/1970 | Driscoll | 568/941 |
| 4,329,522 | 5/1982 | Gilbert et al. | 568/942 |

Primary Examiner—Leland A. Sebastian
Assistant Examiner—T. J. Wallen
Attorney, Agent, or Firm—Anthony T. Lane; Robert P. Gibson; Edward F. Constigan

[57] ABSTRACT

A composition comprising 1,4,6,9-tetranitrodiamantane, and process for its preparation are disclosed.

7 Claims, No Drawings

1,4,6,9-TETRANITRODIAMANTANE

GOVERNMENTAL INTEREST

The invention described herein may be manufactured, used and licensed by or for the Government for Governmental purposes without payment to me of any royalties thereon.

BACKGROUND OF INVENTION

1. Field of Invention

This invention relates to an improved solid fuel or fuel component for use in missiles and rockets.

More particularly, this invention relates to 1,4,6,9-tetranitrodiamantane and a process of making the same.

2. Description of Prior Art 1,4,6,9-Tetranitrodiamantane (TND) is useful as an improved solid fuel or solid fuel component for missiles and rockets. In comparison to the dinitroalkyladamantanes, known fuels, TND is also a crystalline solid and can also be employed with suitable oxidants such as ammonium nitrate and potassium perchlorate as a solid fuel. However TND is more advantageous because of the larger amount of oxygen in its structure available for recombination during combustion. TND is more advantageous for the cited use becase it is a nonexplosive, energetic material with exceptional thermal stability. A comparison of the oxygen balance of known fuels with TND is as follows:

| Oxygen Balance | |
| --- | --- |
| Dinitroalkyladamantanes | −173 to −199 |
| Dinitroadamantane | −163 |
| 1,4,6,9-tetranitrodiamantane | −121.7 |
| 1,3,5,7-tetranitroadamantane | −91 |

Thus, as shown above, TND has improved combustibility as compared to dinitroadamantanes. Also, since 1,3,5,7-tetranitroadamantane has explosive properties and is classed as an explosive, it is less advantageous than TND for use as a fuel or fuel component because of the additional hazard inherent in its use.

SUMMARY OF THE INVENTION

It is an object of this invention to provide a non-explosive, energetic material which has exceptional thermal stability for use as a solid fuel or solid fuel component.

Another object is to provide a non-explosive, energetic composition of matter having improved combustibility for use as a solid fuel or solid fuel component.

A further object is to provide a novel composition of matter, 1,4,6,9-tetranitrodiamantane having an oxygen balance of −121.7.

In general, the novel composition of matter, 1,4,6,9-tetranitrodiamantane has the following structure:

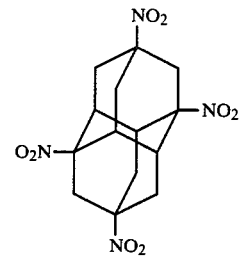

The diamantane of this invention has an oxygen balance of −121.7. The oxygen balance is a measure of the fuel/oxygen ratio in a given compound. It is an index of the deficiency or excess of oxygen in the compound required to convert all the carbon in the comound to carbon dioxide, and all the hydrogens to water (reference is made to the Encyclopedia of Explosives and Related Items, S. M. Kay, ed., U.S. Army ARRADCOM, Dover, N.J., Vol. 8, P. 057 (1978).

We have prepared 1,4,6,9-tetranitrodiamantane in the following sequences of procedures.

Preparation of 1,4,6,9-Tetraiododiamantane

Iodine (2.8 g; 11.1 mmol) was added to small pieces of aluminum foil (1.2 g; 44.4 mmol) in a reaction flask and the mixture was stirred at 80° until part of the iodine vaporized coating the foil. Carbon disulfide (100 ml), which was previously dried over molecular sieves, was added through the top of the reflux condenser into the reaction flask, and the mixture was stirred under reflux for 1 hour in a bath at 60° C. The mixture was cooled to room temperature, 1,4,6,9-tetrabromodiamantane (2.4 g; 4.77 mmol) prepared according to the method of P. v. R. Schleyer et al, J. Org. Chem, Vol. 39, 2995 (1974), was added, and the mixture was stirred 3 hrs. at room temperature. The mixture was quenched in a cold-water bath with 15 ml of 10% aqueous sodium bisulfite, and the aggregate passed through a filter with suction. The filter cake was stirred in 5% aq. hydrochloric acid without heating to remove the aluminum. Filtration and washing first with water, then with methanol yielded 2.7 g of product corresponding to a yield of 82% of theory based on the tetrabromo starting material. For analysis, a sample was crystallized from toluene as a white powder showing no melting to 390° C. (with decomposition).

Analysis: Calculated for $C_{14}H_{16}I_4$: C, 24.30; H, 2.33; I, 73.36. Found: C 24.52; H, 2.43; I, 73.07.

Preparation of 1,4,6,9-Tetraacetamidodiamantane

In a cylindrical quartz reaction vessel approximately two inches in diameter, equipped with a condenser, agitator and heating mantle, 1,4,6,9-tetraiododiamantane (2.0 g; 2.9 mmol) was stirred briskly in 500 ml of acetonitrile (0.07–0.1% water content) to which 0.4 ml of water had been added. The resulting mixture was photolyzed for 120 hours under reflux in a Rayonet Photochemical Reactor containing 16 lamps, each lamp approximately 0.03 watt, 1849 angstroms and 2.2 watts, 2537 angstroms (manufacturer's literature, the Southern New England Ultraviolet Co., Middletown, CT). The reaction mixture was filtered to remove the gray powdery solids. Washing with fresh acetonitrile and air drying yielded 0.84 g of product, corresponding to a yield of 70% of theory based on the tetraiodo starting material.

The product, showing no melting to 400° C. was largely insoluble in water, methanol, acetone, dimethyl formamide, and toluene. The IR spectrum (KBr) showed N-H stretching at 3300 cm$^{-1}$.

Preparation of 1,4,6,9-Tetraaminodiamantane Tetrahydrochloride 1,4,6,9-tetraacetamidodiamantane (1.0 g; 2.5 mmol) was refluxed for 18 hours in 60 ml of concentrated hydrochloric acid diluted with an equal volume of water. The clear, yellow solution was evaporated in a rotary evaporator, and the residual solids were taken up in methanol. The undissolved powdery solids were collected in a filter, washed with methanol and dissolved in a minimal quantity of water. Filtration and dilution of the filtrate with acetone yielded 0.7 g (71% of theory) showing no melting to 360° C. The IR spectrum (KBR) showed $_N$+-H stretching at 2900 cm$^{-1}$.

Preparation of 1,4,6,9-Tetranitrodiamantane 1,4,6,9-tetraaminodiamantane tetrahydrochloride (0.67 g; 1.7 mmol) was dissolved in 25 ml of water, and converted to the free base by addition of an equivalent amount of aqueous sodium hydroxide. Magnesium sulfate (1.2 g; 10.0 mmol) was added and the agitated mixture was diluted with 10 ml of acetone. Potassium permanganate (6.6 g; 40.8 mmol) was added portionwise with agitation during 20 min. The reaction mixture was then warmed to 30° C., and agitated at that temperature for 48 hrs., and then filtered. The filter cake was washed with water, then dried and extracted twice with 75 ml portions of boiling toluene. The combined extracts were gravity filtered, and concentrated to approximately 30 ml and cooled to yield 0.1 g of granular, crystalline product. The filtrate yielded an additional 0.1 g of product for a total yield of 0.2 g, 32% of theory. For analysis, a sample of the product was dissolved in boiling acetone and precipitated as a powder from solution by the addition of water. The product had the following properties: mp. 368°-370° C. (with decomposition); NMR (DMSO-D$_6$δ2.20 [4H, s, CH (b)], 2.38 [4H, s, CH (D)], 2.75 [4H, s, CH$_2$(a)], 3.32 [4H, s, CH (c)] relative to TMS(3); mass spectrum, m/e 368 [M+, 100%], 322 [M-NO$_2$)+, 75%], 246 [M-2NO$_2$-NO]+, 32%), 230 [M-3NO$_2$)+, 34%]; IR (KBR) 1545, 1367 cm$^{-1}$ (NO$_2$). Elemental analysis: Calculated for C$_{14}$H$_{16}$N$_4$O$_8$: C, 45.66; H, 4.38; N, 15.21. Found: C, 45.30; H. 4.50; N. 14.80.

The foregoing data prove that the product is 1,4,6,9-tetranitrodiamantane. Thus, the infrared spectrum showed peaks for nitro groups in the expected range. The NMR spectrum showed four types of proton, as expected. The mass spectrum was consistent with a structure containing four nitro groups, and with the molecular weight of the compound. The elemental analysis agreed closely with the calculated values.

Thermal Stability: 1,4,6,9-tetranitrodiamantane has a melting point of 368° C.-370° C., and although accompanied by decomposition, there is no darkening below 250° C.

Impact Sensitivity: "No-go" in the range of 150-240 cm. This test ("ERL type-12 Tooling") is described in the "Manual of Sensitivity Tests", G. R. Walker, Ed., Canadian Armament Research and Development Establishment, February 1966, page 15. Accordingly, as the results indicate, the novel compound is insensitive to impact and is safe to handle.

Detonation: A 36 mg sample was pressed at a loading pressure of 11K psi into a steel washer, 0.125" and 0.125" thick. The sample, in the washer, was placed on a 1"×1"×½" steel block, and initiated by an XM70 electrically fired detonator (Picatinny Arsenal Technical Report No. 3209, "Development of TX6025 and XM70 Electric Detonators", Ruth Trezona, December 1964). The test produced a dent 0.0085" deep, and no enlargement of the washer, the same as the blank test using a standard inert powder with the same detonator. This shows that the composition of this invention is non-explosive.

Also, U.S. Pat. No. 3,535,390 discloses solid fuels for rockets containing dinitroalkyladamantanes in admixture with ammonium nitrate or potassium perchlorate. The compound of this invention is more efficient energetically than the dinitroalkyladamantanes because of its oxygen balance, and hence is more effective for such use.

I claim:
1. 1,4,6,9-tetranitrodiamantane.
2. A process for preparing 1,4,6,9-tetranitrodiamantane which comprises reacting 1,4,6,9-tetraminodiamantane tetrahydrochloride with an oxidizing agent.
3. The process of claim 2 wherein the oxidizing agent is potassium permanganate.
4. The process of claim 2 wherein said 1,4,6,9-tetraminodiamantane tetrahydrochloride is prepared by treating 1,4,6,9-tetraacetamidodiamantane with acid.
5. The process of claim 4 wherein said acid is hydrochloric acid.
6. The process of claim 4 wherein said 1,4,6,9-tetraacetamidodiamantane is prepared by photolyzing 1,4,6,9-tetraiododiamantane in the presence of acetonitrile.
7. The process of claim 6 wherein said 1,4,6,9-tetraiododiamantane is prepared by treating 1,4,6,9-tetrabromodiamantane with iodine in the presence of aluminum.

* * * * *